United States Patent
Kim et al.

(10) Patent No.: US 8,018,581 B2
(45) Date of Patent: Sep. 13, 2011

(54) APPARATUS AND METHOD FOR ANALYZING MILK IN FIELD

(75) Inventors: Hyun Seob Kim, Suwon-si (KR); Sang Bum Kim, Cheonan-si (KR); Kwang Sook Ki, Cheonan-si (KR); Hyun June Lee, Pyeongtaek-si (KR); Won Mo Cho, Suwon-si (KR)

(73) Assignee: Republic of Korea (Management: Rural Development Administration), Gyeonggi-do (KR)

( * ) Notice: Subject to any disclaimer, the term of this patent is extended or adjusted under 35 U.S.C. 154(b) by 325 days.

(21) Appl. No.: 12/353,667

(22) Filed: Jan. 14, 2009

(65) Prior Publication Data

US 2009/0180102 A1    Jul. 16, 2009

(30) Foreign Application Priority Data

Jan. 14, 2008  (KR) .................. 10-2008-0003729

(51) Int. Cl.
*G01N 21/00* (2006.01)
*G01N 21/25* (2006.01)
(52) U.S. Cl. ........... 356/72; 356/418; 356/331; 356/326
(58) Field of Classification Search .......... 356/72, 356/418, 331, 332, 326; 250/338.1, 339.06
See application file for complete search history.

(56) References Cited

U.S. PATENT DOCUMENTS

| 3,861,788 | A | 1/1975 | Webster ............. 350/315 |
| 4,082,464 | A | 4/1978 | Johnson, Jr. ............. 356/188 |
| 4,236,075 | A | 11/1980 | Nexo et al. ............. 250/343 |
| 5,343,044 | A | 8/1994 | Sjaunja et al. |
| 5,519,219 | A | 5/1996 | Alexay et al. ............. 250/339.07 |
| 6,517,778 | B1 * | 2/2003 | Kumar et al. ............. 422/82.05 |
| 7,840,360 | B1 * | 11/2010 | Micheels et al. ............. 702/25 |
| 2005/0233037 | A1 | 10/2005 | Bendtsen et al. |

FOREIGN PATENT DOCUMENTS

| EP | 1666870 A2 | 6/2006 |
| JP | 55-29784 | 3/1980 |
| JP | 4-47254 | 2/1992 |
| JP | 11-503236 | 3/1999 |
| JP | 2002-122538 | 4/2002 |

* cited by examiner

*Primary Examiner* — L. G Lauchman
(74) *Attorney, Agent, or Firm* — Ladas & Parry, LLP

(57) ABSTRACT

Disclosed are an apparatus and a method for analyzing milk in a field, capable of analyzing the quality of milk by rapidly and easily examining components of milk in a field, other than a laboratory. To manage the quality of milk, a monochromator using an interference filter having different wavelength bands is employed to the apparatus for analyzing milk, and the amount of milk samples used at one time is increased, so components of milk are simultaneously examined. The apparatus for analyzing milk has a portable structure, so the components of milk are simply, rapidly and easily determined in the field, and the apparatus for analyzing milk is inexpensive as compared with existing apparatuses, thereby increasing the productivity.

4 Claims, 13 Drawing Sheets

(BEFORE MOUNTING SAMPLE)        (AFTER MOUNTING SAMPLE)

A

B

C

D

APPARATUS AND METHOD FOR ANALYZING MILK IN FIELD

CROSS-REFERENCE TO RELATED APPLICATION

This application claims the benefit of Korean Patent Application No. 10-2008-0003729 filed on Jan. 14, 2008, in the Korean Intellectual Property Office, the disclosure of which is incorporated herein by reference.

BACKGROUND OF THE INVENTION

1. Field of the Invention

The present invention relates to an apparatus and a method for analyzing milk in a field. More particularly, the present invention relates to an apparatus and a method for analyzing milk for a field, capable of analyzing the quality of milk by rapidly and easily examining components of milk in a field, other than a laboratory.

2. Description of the Related Art

In general, in order to manage the quality of milk, components related to the milk quality are examined by using various measurement devices, and measured data obtained through the examination serves as a reference value to determine the quality of milk.

A conventional apparatus for analyzing milk is used for examining the components such as milk protein, milk sugar, etc., which are used to determine the quality of milk. The conventional apparatus has a wavelength band of about 400 to 2500 nm and includes a grating for scanning the wavelength of 400 to 2500 nm, so that the measurement time is substantially increased and the operational method is complicated.

In addition, the conventional apparatus for analyzing milk is manufactured suitably for the laboratory, so that the conventional apparatus for analyzing milk is mainly used for the laboratory. However, the conventional apparatus for analyzing milk is very sensitive, so it cannot be used in the field. In addition, since a sample cell has a size of 1 mm, an introduction of the sample cell is very difficult in the conventional apparatus for analyzing milk.

Further, since the amount of introduced sample cells is very small, the measurement must be performed several times in order to examine various components of milk.

In addition, the equipment for determining the quality of milk is very expensive laboratory equipment, so a laboratory must be provided to install the equipment. As described above, the conventional apparatus for analyzing milk has various disadvantages when it is used in the field.

SUMMARY OF THE INVENTION

Accordingly, it is an aspect of the present invention to provide an apparatus and a method for analyzing milk in a field, in which the operation of the apparatus is simple and easy, and the measurement is performed with high precision, so that components of milk is directly examined in the field, thereby rapidly determining the quality of milk. In addition, the amount of samples introduced at one time is increased, so that various components can be simultaneously examined, thereby minimizing the measurement time.

Additional aspects and/or advantages of the invention will be set forth in part in the description which follows and, in part, will be apparent from the description, or may be learned by practice of the invention.

The foregoing and and/or other aspects of the present invention are achieved by providing an apparatus for analyzing milk by examining specific components of milk. The apparatus includes a body connected to a power supply unit installed at an outside of the body, provided at an outer surface thereof with a monitor for outputting measured data, a power button for turning on/off power and an operating button for run, and formed at an upper end thereof with a cell introduction hole through which a sample cell is inserted, a lamp power, which is installed in the body and operates when the operating button is switched on, a plurality of lamp fixing brackets, which are installed in the body and equipped with halogen lamps connected to the lamp power to generate beam, a sample fixing part, which is disposed corresponding to the cell introduction hole and is mounted in the lamp fixing bracket to mount the sample cell thereon, a monochromator, which is mounted at a side of the sample fixing part and includes a filter slit type tube having slits formed at both sides thereof to allow a predetermined amount of beam to pass therethrough, a rotary plate, which is provided with a plurality of interference filters and is installed in the filter slit type tube, and a drive motor connected to the rotary plate, a detector, which is mounted at a rear surface of the filter slit tube to detect incident monochromatic light, and a processing unit, which is connected to the detector to transfer an electric signal output from the detector to the monitor as data.

It is another aspect of the present invention to provide a method for analyzing milk by examining specific components of milk, the method includes filling a milk sample in a sample cell to fix the milk sample to a sample fixing part and then irradiating beam of a halogen lamp to the milk sample through a lamp power, monochromating the beam of the halogen lamp, which has passed through the milk sample, by allowing the beam to pass through a plurality of interference filters of the rotary plate, transferring the monochromated beam to a detector and processing a signal of the monochromated beam output from the detector in a processing unit, and outputting data, which is output from the processing unit, through a monitor.

As described above, according to the apparatus and the method for analyzing milk in the field of the present invention, the monochromator using an interference filter having different wavelength bands is employed, and the amount of milk samples used at one time is increased, so milk protein, milk sugar, somatic cells butterfat, MUN (milk urea nitrogen), total solids, antibiotics, melamine, etc. can be simultaneously examined.

In addition, the apparatus for analyzing milk according to the present invention has a portable structure, so the components of milk can be simply, rapidly and easily determined in the field, instantly. In addition, the apparatus for analyzing milk according to the present invention is inexpensive as compared with existing apparatuses, thereby increasing the productivity.

Therefore, the apparatus and the method for analyzing milk according to the present invention can provide more fresh milk as compared with the conventional apparatus and the method for analyzing milk, so customers are satisfied, thereby promoting milk consumption. Further, if the apparatus and the method for analyzing milk according to the present invention are applied to milking cow farming, functional milk can be produced at a low price.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE PREFERRED EMBODIMENTS

Figure 1:
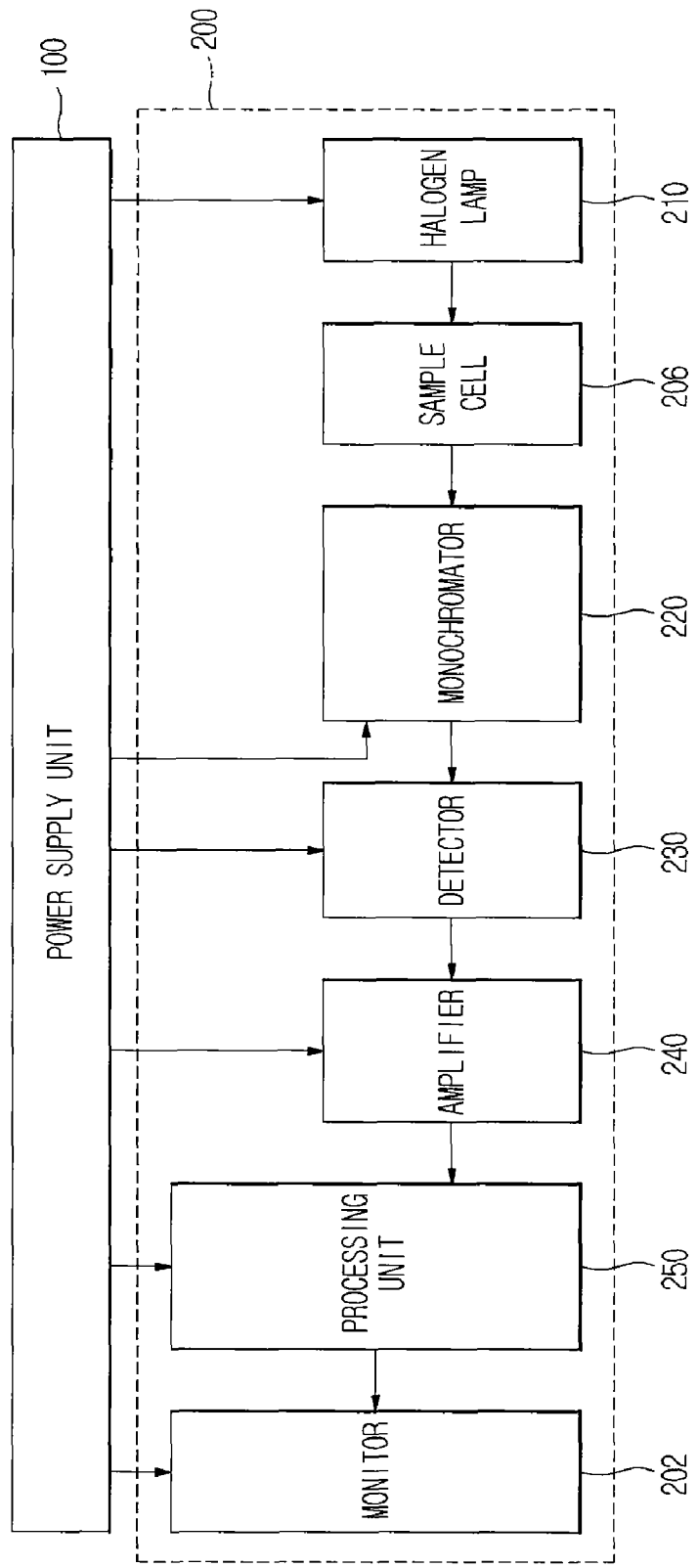
FIG. 1 is a block diagram representing a configuration of an apparatus for analyzing milk in the field according to an embodiment of the present invention.

Reference will now be made in detail to the embodiments of the present invention, examples of which are illustrated in the accompanying drawings, wherein like reference numerals refer to the like elements throughout. The embodiments are described below to explain the present invention by referring to the figures.

Figure 2:
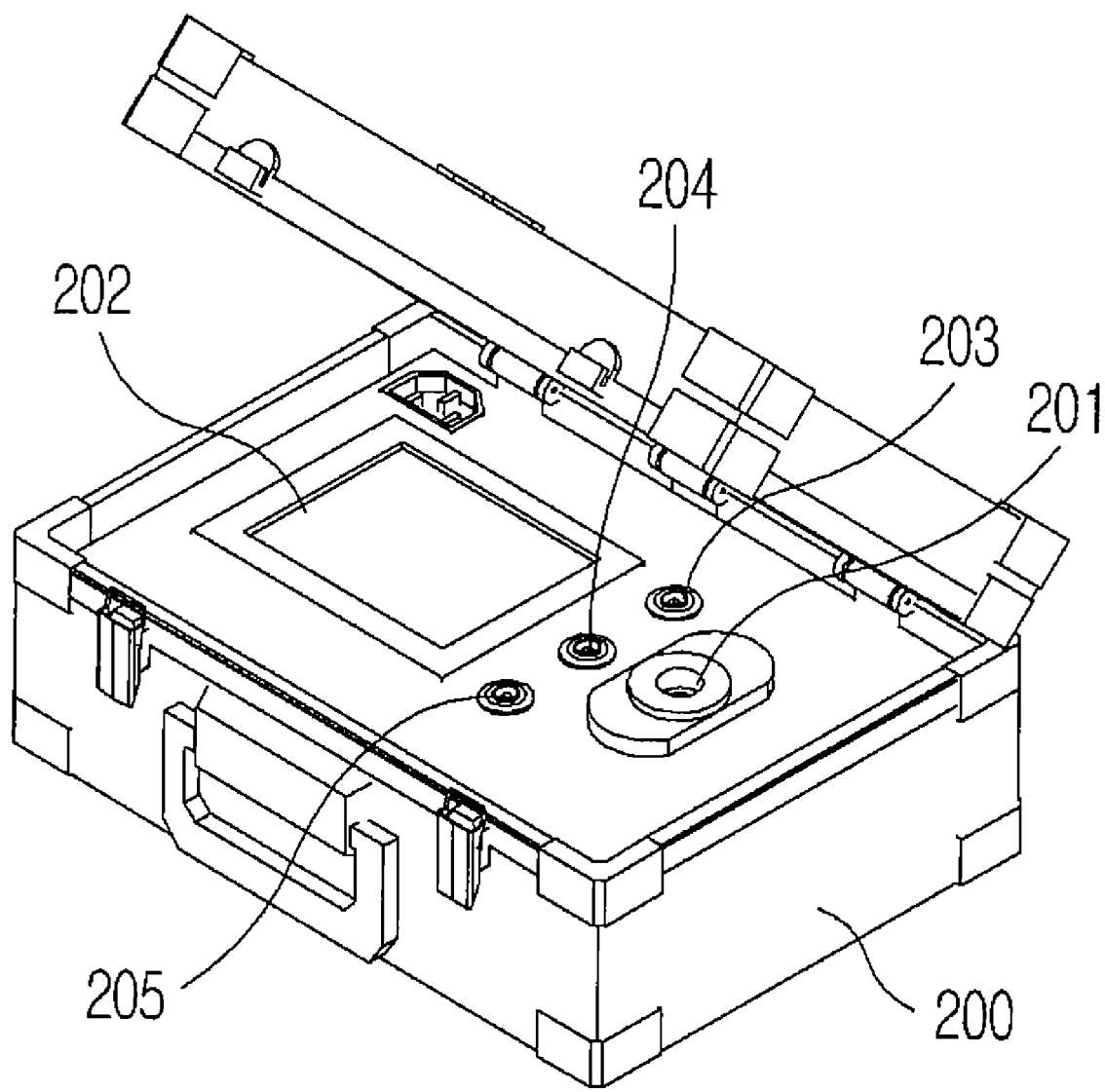
FIG. 2 is a perspective view representing an external appearance of the apparatus for analyzing milk in the field according to the embodiment of the present invention.
Figure 3:
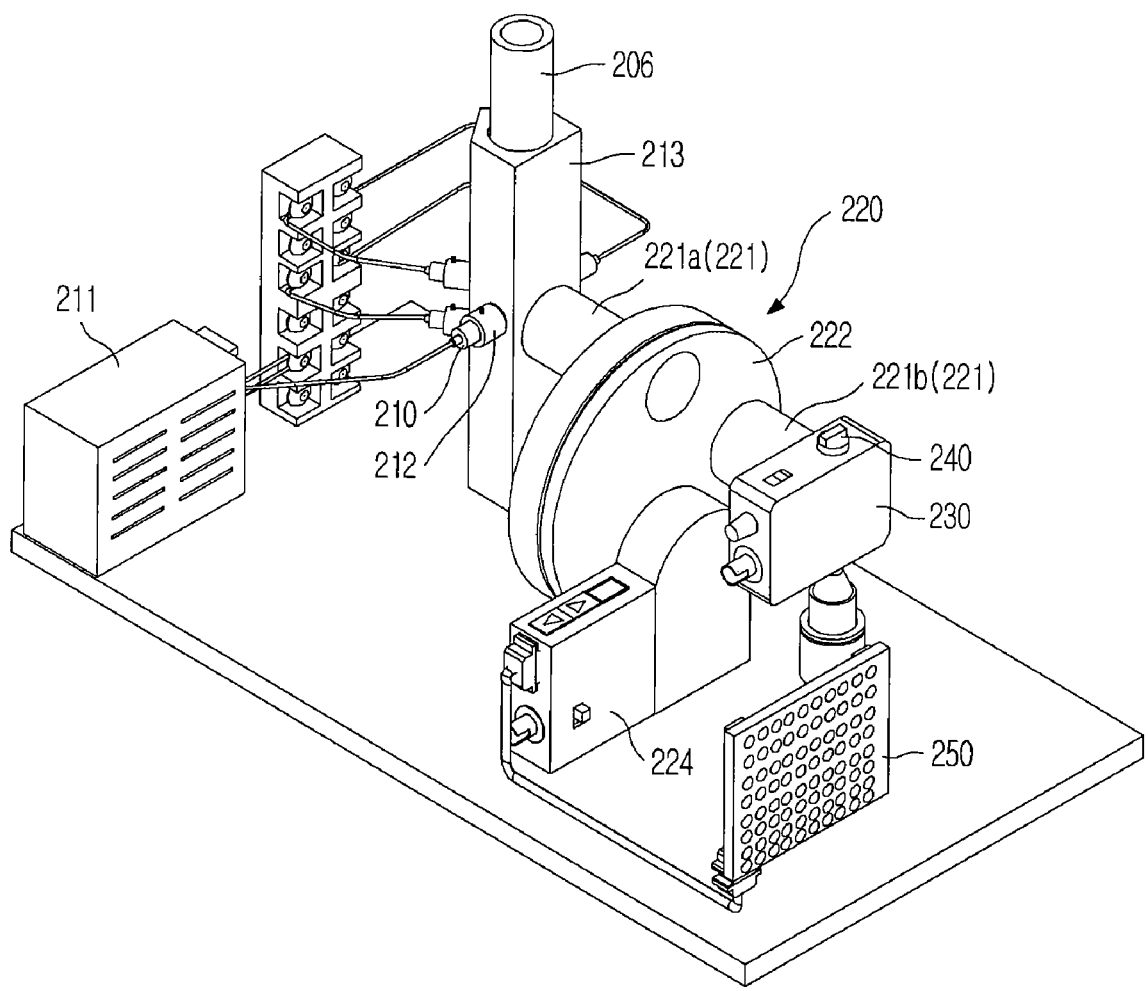
FIG. 3 is a perspective view representing an interior of a body of the apparatus for analyzing milk in the field including a filter-type monochromator according to the embodiment of the present invention.
Figure 4:
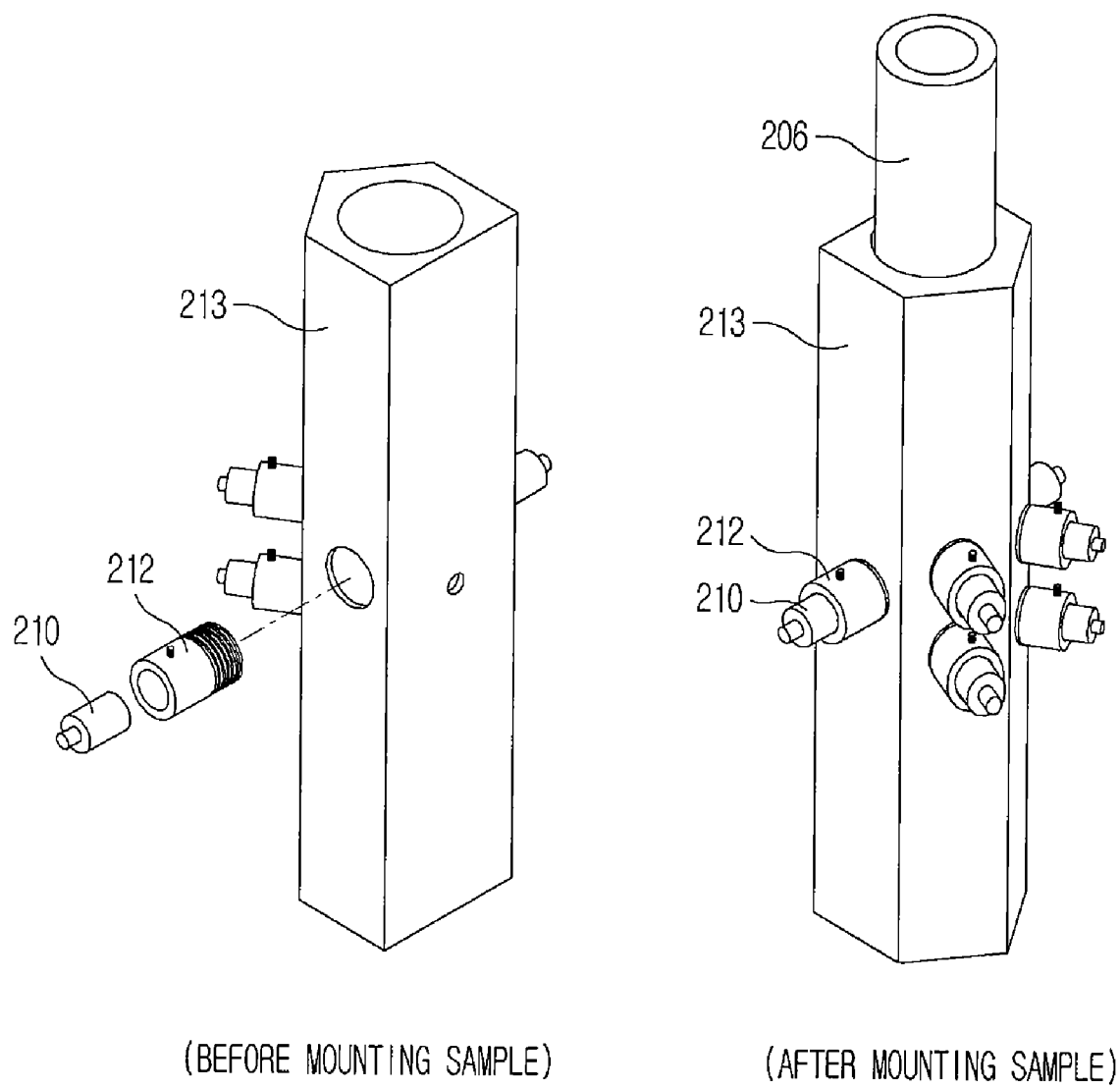
FIG. 4 is an enlarged perspective view representing a sample fixing part according to the embodiment of the present invention.
Figure 5:
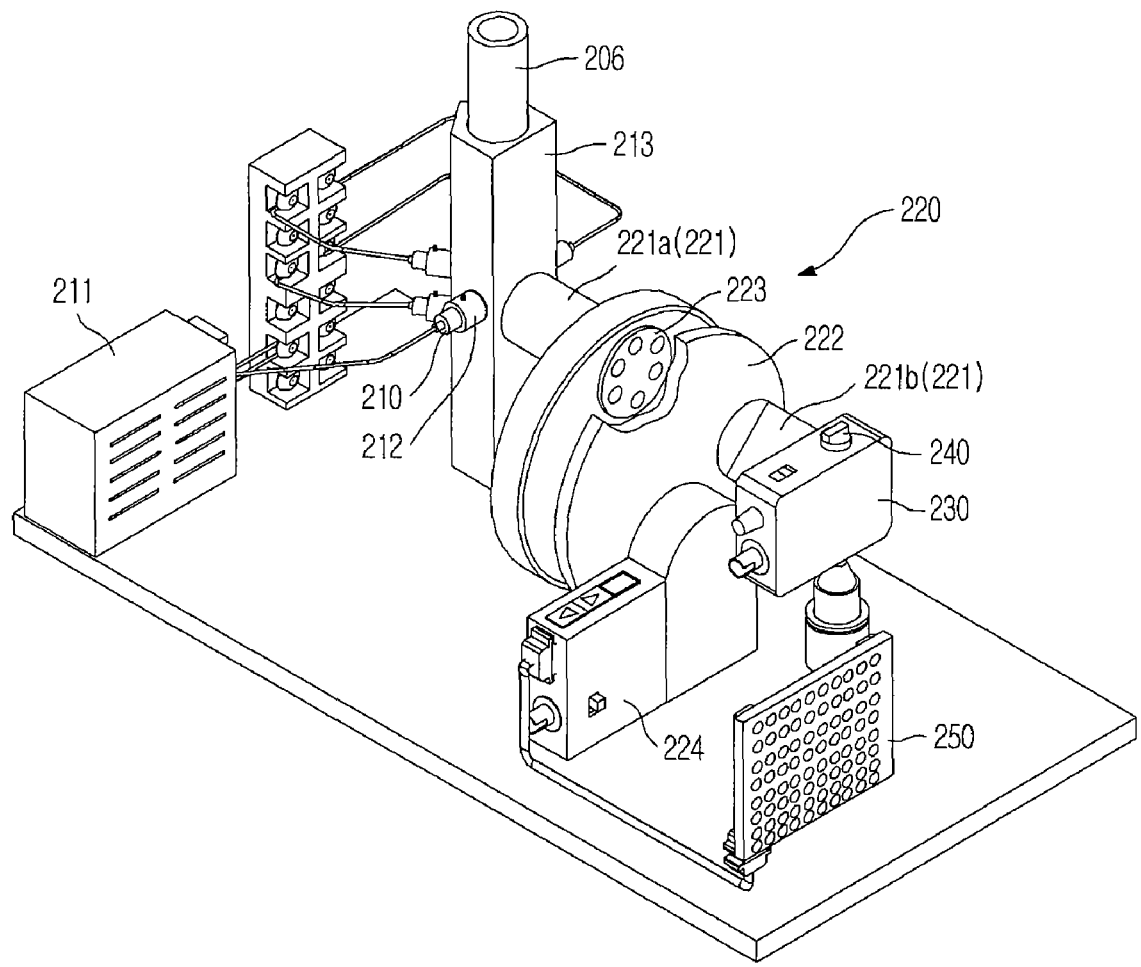
FIG. 5 is an exploded and enlarged perspective view representing a monochromator according to the embodiment of the present invention.

FIG. 1 is a block diagram representing a configuration of an apparatus for analyzing milk in the field according to an embodiment of the present invention, FIG. 2 is a perspective view representing an external appearance of the apparatus for analyzing milk in the field according to the embodiment of the present invention, FIG. 3 is a perspective view representing an interior of the apparatus for analyzing milk in the field according to the embodiment of the present invention, FIG. 4 is an enlarged perspective view representing parts of the apparatus according to the embodiment of the present invention, and FIG. 5 is an exploded view representing parts of the apparatus according to the embodiment of the present invention.

The apparatus for analyzing milk in the field according to the present invention uses a monochromator 220 to which interference filters 223 having different wavelength bands are applied to measure components of milk corresponding to specific wavelength bands of the interference filters 223, thereby simultaneously measuring various components of milk.

The apparatus for analyzing milk in the field according to an embodiment of the present invention mainly includes a power supply unit 100 and a body 200. The power supply unit 100 according to the embodiment is additionally provided outside the body 200 to minimize the influence of the power supply unit 100 exerted on the body 200, thereby maximizing the electrical stability.

As shown in FIG. 2, a monitor 202 provided in the form of an LCD screen is mounted at an outer surface of the body 200 to output a final result. Adjustment buttons are divided into a power button 203 for turning on/off the apparatus, an operating button 204 for run and a printing button 205 used when a data result output on the monitor 202 is printed out. The adjustment buttons are installed at an outer surface of the body 200.

As shown in FIG. 3, a halogen lamp 210, the monochromator 220, a detector 230, an amplifier 240, a processing unit 250, etc. are provided inside the body 200.

FIG. 4 is an enlarged perspective view partially representing the interior of the body of the apparatus for analyzing milk using a filter-type monochromator according to the present invention, in which six halogen lamps 210 are provided in the body 200 to obtain stable data and each halogen lamp 210 is mounted on a lamp fixing bracket 212 at a side of a sample fixing part 213.

A test tube type sample cell 206 containing a milk sample is mounted on the sample fixing part 213. As shown in FIG. 4, the sample fixing part 213 has a rectangular shape, so that four halogen lamps 210 are disposed in front of the interference filter 223 and the remaining two halogen lamps 210 are disposed at a position that is rotated at about 90 degrees relative to the interference filter 223. That is, the sample fixing part 213 is mounted between the lamp fixing bracket 212 and the monochromator 220 such that the sample fixing part 213 is disposed at an inner side of the lamp fixing bracket 212.

In addition, a cell introduction hole 201 is formed through at an upper part of an outer surface of the body 200 corresponding to the sample fixing part 213 such that the sample cell 206 is inserted into the cell introduction hole 201.

According to the embodiment of the present invention, the sample cell 206 is prepared in a size of 20 mm in use, so that a relatively large quantity of milk samples can be introduced at one time. Accordingly, a plurality of halogen lamps 210 are provided such that the beam is irradiated onto the sample cell 206 in various directions.

Meanwhile, since a lamp power 211 for turning on the halogen lamp 210 is mounted in the body 200, if the operating button 204 is switched on, the halogen lamp 210 is operated by the lamp power 211.

The monochromator 220 includes a filter slit type tube 221a and 221b having filter slits formed at a front surface and a rear surface thereof, respectively, a rotary plate 222 provided in the tube, and a drive motor 224 for rotating the rotary plate 222. Six interference filters 223 are arranged on the rotary plate 222 in a circumference direction of the rotary plate 222 to filter beam having various wavelength bands.

The interference filters 223 are set to filter beams having wavelengths of 830 nm, 850 nm, 880 nm, 930 nm, 1200 nm (long pass filter) and 1100 nm (short pass filter) having a close relation with milk protein, milk sugar, somatic cells, butterfat, MUN (milk urea nitrogen), total solids, antibiotics, melamine, etc., which are necessary for analyzing the milk such that the total components of milk can be measured.

In other words, each interference filter 223 is applied to each component necessary for analyzing the milk, and weight is set with respect to the six representative wavelengths, so the weight is defined as a constant corresponding to each component.

Meanwhile, the detector 230 is installed at a rear surface of the filter slit type tube 221b such that a beam monochromated through the interference filter 223 passes through the detector 230 and converted into an electric signal.

The electric signal is uniformly amplified by the amplifier 240 connected to the detector 230, and data is output on the monitor 202 provided at the outer surface of the body 200 through the processing unit 250 connected to the amplifier 240.

As described above, according to the present invention, many components of milk can be simultaneously measured and analyzed through a simple operation, which is performed by filling the sample cell 206 with the milk sample and fixing the sample cell 206 to the sample fixing part 213, and then pushing the power button 203 and the operating button 204. In addition, since the apparatus for analyzing milk can be used in practice, the quality of milk can be simply and rapidly analyzed in various fields dealing with milk, such as a milking cow farm house, a manufacturer of dairy product, a mart, etc.

Hereinafter, an operation of the apparatus for analyzing milk according to the embodiment of the present invention will be described.

A standard value is set by measuring components of water serving as a reference cell before the components of milk are measured.

Milk to be subject to the quality analysis is selected and then filled in the sample cell 206. Then, the sample cell 206 is input through the cell introduction hole 201 of the body 200 and fixed to the sample fixing part 213.

Then, power is supplied to the body 200 through the power supply unit 100, and the power button 203 of the body 200 is pressed for switch-on and then the operating button 204 is pressed.

Accordingly, the lamp power 211 is turned on to supply power to the halogen lamp 210, so that the halogen lamp 210 generates a beam.

As the beam passes through the milk sample contained in the sample cell 206, a predetermined amount of beam is introduced through the slit of the filter slit type tube 220a, so that dispersed light is minimized and the influence of the dispersed light is minimized. The beam, which has passed through the front slit, is monochromated while passing through the interference filter 223 of the rotary plate 222.

At this time, the rotary plate 222 makes one rotation by the drive motor 224 and the interference filter 223 monochromates the beam according to wavelength bands, so that specific components of the milk sample are represented as a spectrum.

While the rotation plate 222 is making one rotation, the six interference filters 223 can measure all components of the milk. Therefore, the operating button 204 is pushed such that the rotary plate 222 makes one rotation.

That is, as the rotary plate 222 makes one rotation, the beam, which has passed through the filter slit type tube 221, is monochromated by the six interference filters 223, thereby producing the spectrums of the milk components corresponding to the wavelength bands.

As described above, the beam monochromated by the interference filter 223 passes through the filter slit type tub 221b formed at the rear surface of the filter bracket 220 and then is introduced into the detector 230. The detector 230 detects the specific components of milk using the monochromated beam introduced into the detector 230.

In this case, since dispersed light is minimized by the filter slit type tubes 221a and 221b, the monochromated light introduced into the detector 230 produces the spectrum corresponding to the wavelength bands of the interference filters 223.

Then, the detector 230 converts the detected specific components into the electric signal and transfers the electric signal to the amplifier 240. The amplifier 240 uniformly amplifies the received electric signal and transfers the amplified signal to the processing unit 250.

After that, the processing unit 250 collects and processes the amplified signal to output data through the monitor 202.

If necessary, the printing button 205 is pushed to print the output data.

The correlation between the measured values of the components of milk, which are measured through monochromation performed by the interference filter 223, and the standard value corresponding to a measured value of water serving as the reference cell is represented by a calibration curve using regression analysis (a linear correlation equation using regression analysis).

A coefficient $R^2$, which corresponds to a coefficient of correlation of the calibration curve and serves as a measure of a linearity, is used as a measure of desirability of the correlation between the measured value of milk and the standard value of water. A standard deviation of the data is represented by using SEC (Standard error of calibration) and SEP (Standard error of prediction).

When the measured value of milk and the standard value of water is represented in the form of a straight line, if data of the measured value of milk and the standard value of water roughly form a predetermined straight line in consideration of $R^2$, SEC and SEP, the correlation between the measured value of milk and the standard value of water is determined to be desirable.

That is, if $R^2$ is nearly 1, and SEC and SEP are nearly 0, the correlation between the measured value of milk and the standard value of water is determined as desirable.

The correlation between the measured value of water and the standard value is represented by using an MLR (Multiple Linear Regression) of the calibration curve.

In addition, a routine analysis is performed using the calibration curve formed through the measured value of milk, and reliability of significance of the routine analysis value is represented by an RMSEP (Root Mean of Standard Error Prediction).

As the reliability significance is checked, the reliability of the value of milk components measured by the signal passing through the interference filters 223 and the values of components actually contained in milk is estimated.

Figure 6:
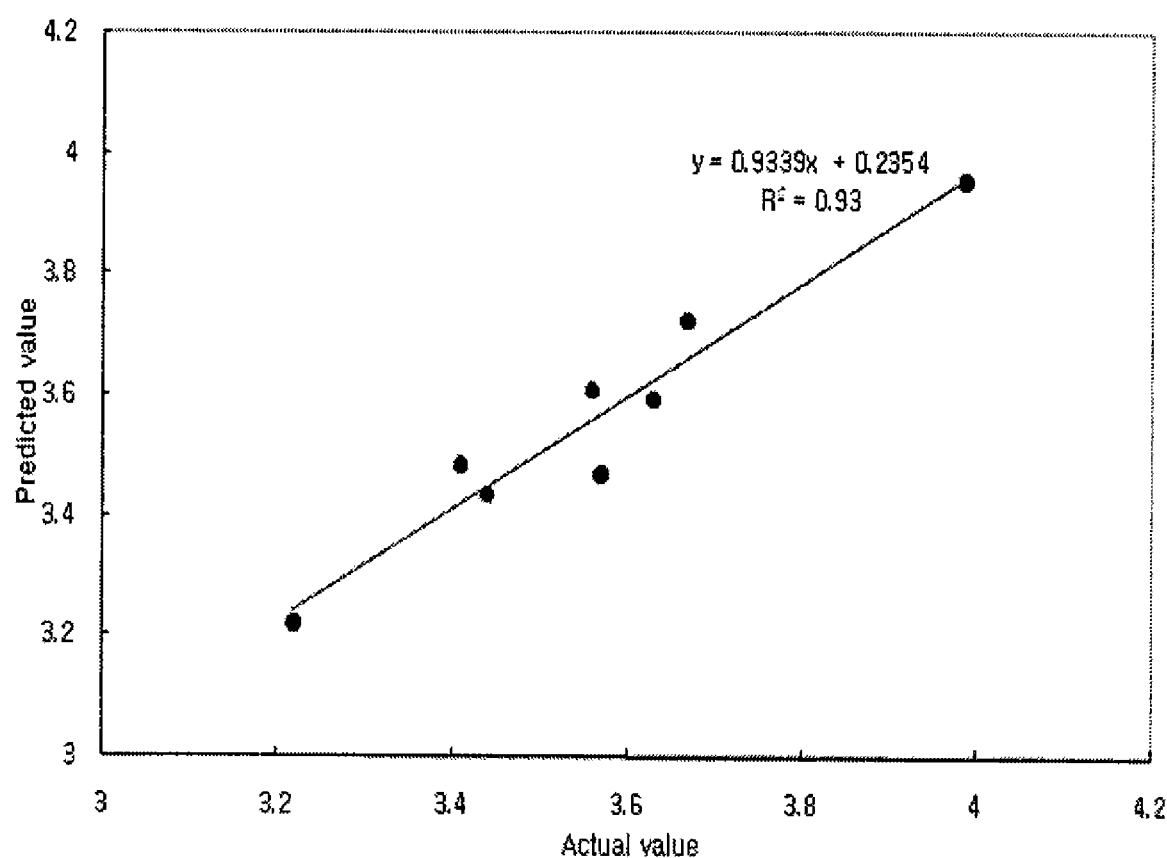
FIG. 6 is a graph representing a result obtained by examining milk protein of milk according to the embodiment of the present invention.

FIG. 6 is a graph representing a result obtained by examining milk protein of milk according to the embodiment of the present invention. Since $R^2$ is 0.93 and the calibration curve has a nearly linear configuration, the measured value of the milk protein is reliable. Therefore, a numerical value of the milk protein of milk can be estimated through the measured value of the milk protein.

Figure 7:
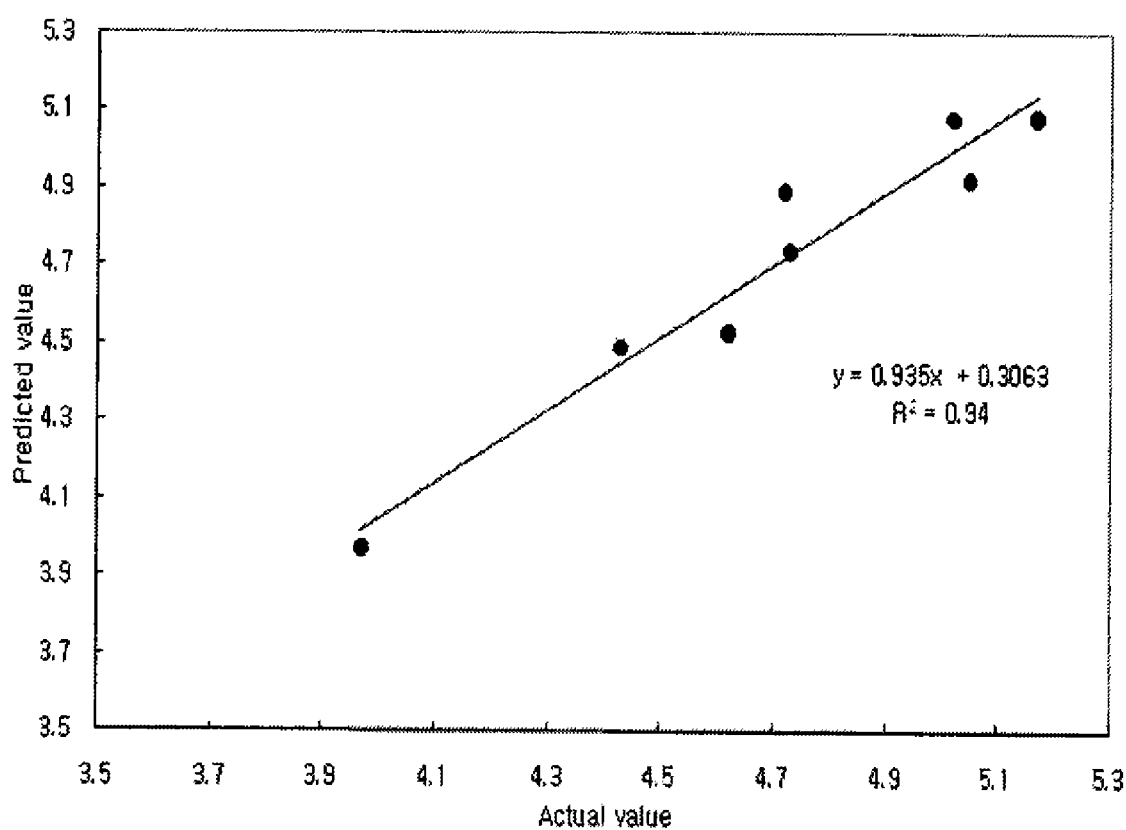
FIG. 7 a graph representing a result obtained by examining milk sugar of milk according to the embodiment of the present invention.

FIG. 7 is a graph representing a result obtained by examining milk sugar of milk according to the embodiment of the present invention. Since $R^2$ is 0.94 and the calibration curve has a nearly linear configuration, the measured value of the milk sugar is reliable. Therefore, a numerical value of the milk sugar of milk can be estimated through the measured value of the milk sugar.

Figure 8:
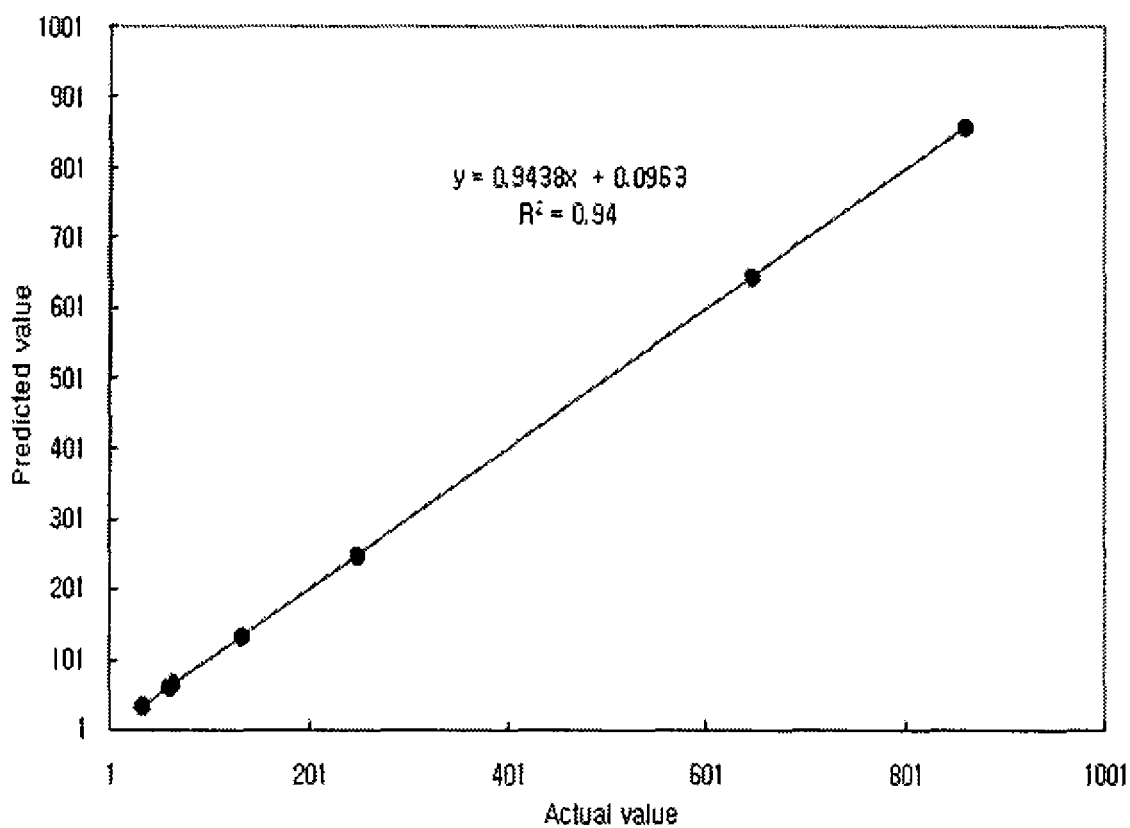
FIG. 8 a graph representing a result obtained by examining somatic cell of milk according to the embodiment of the present invention FIG. 9 a graph representing a result obtained by examining butterfat of milk according to the embodiment of the present invention.

FIG. 8 is a graph representing a result obtained by examining somatic cell of milk according to the embodiment of the present invention. Since $R^2$ is 0.94 and the calibration curve has a nearly linear configuration, the measured value of the somatic cell is reliable. Therefore, a numerical value of the somatic cell of milk can be estimated through the measured value of the somatic cell.

Figure 9:
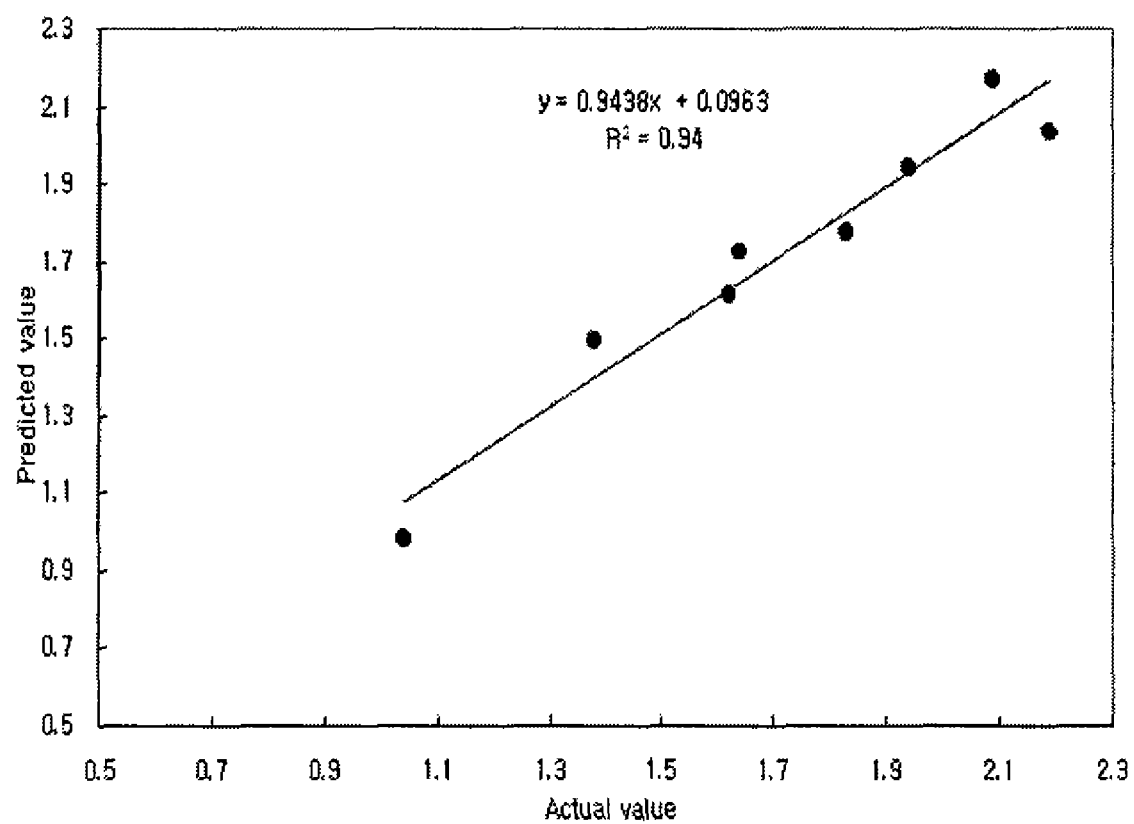

FIG. 9 is a graph representing a result obtained by examining butterfat of milk according to the embodiment of the present invention. Since $R^2$ is 0.94 and the calibration curve has a nearly linear configuration, the measured value of the butterfat is reliable. Therefore, a numerical value of the butterfat of milk can be estimated through the measured value of the butter fat.

Figure 10:
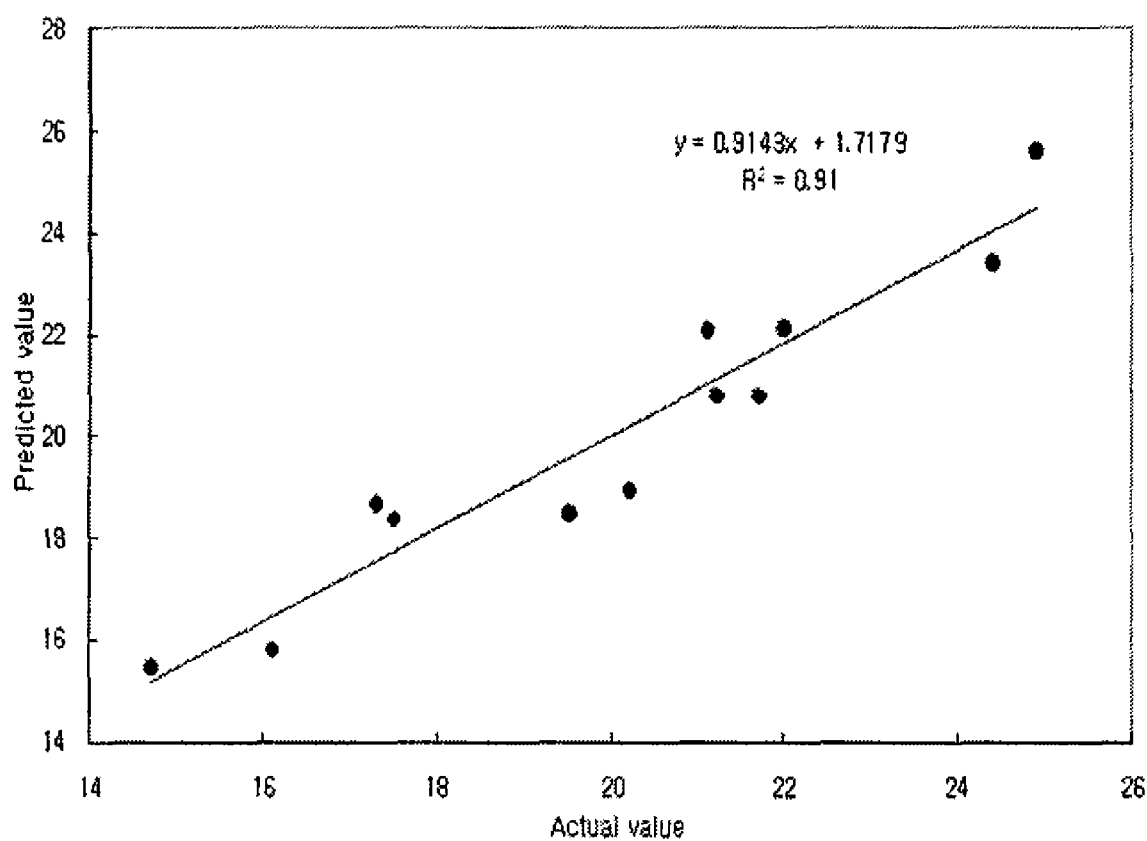
FIG. 10 a graph representing a result obtained by examining MUN of milk according to the embodiment of the present invention.

FIG. 10 is a graph representing a result obtained by examining MUN of milk according to the embodiment of the present invention. Since $R^2$ is 0.91 and the calibration curve has a nearly linear configuration, the measured value of the MUN is reliable. Therefore, a numerical value of the MUN of milk can be estimated through the measured value of the MUN.

Figure 11:
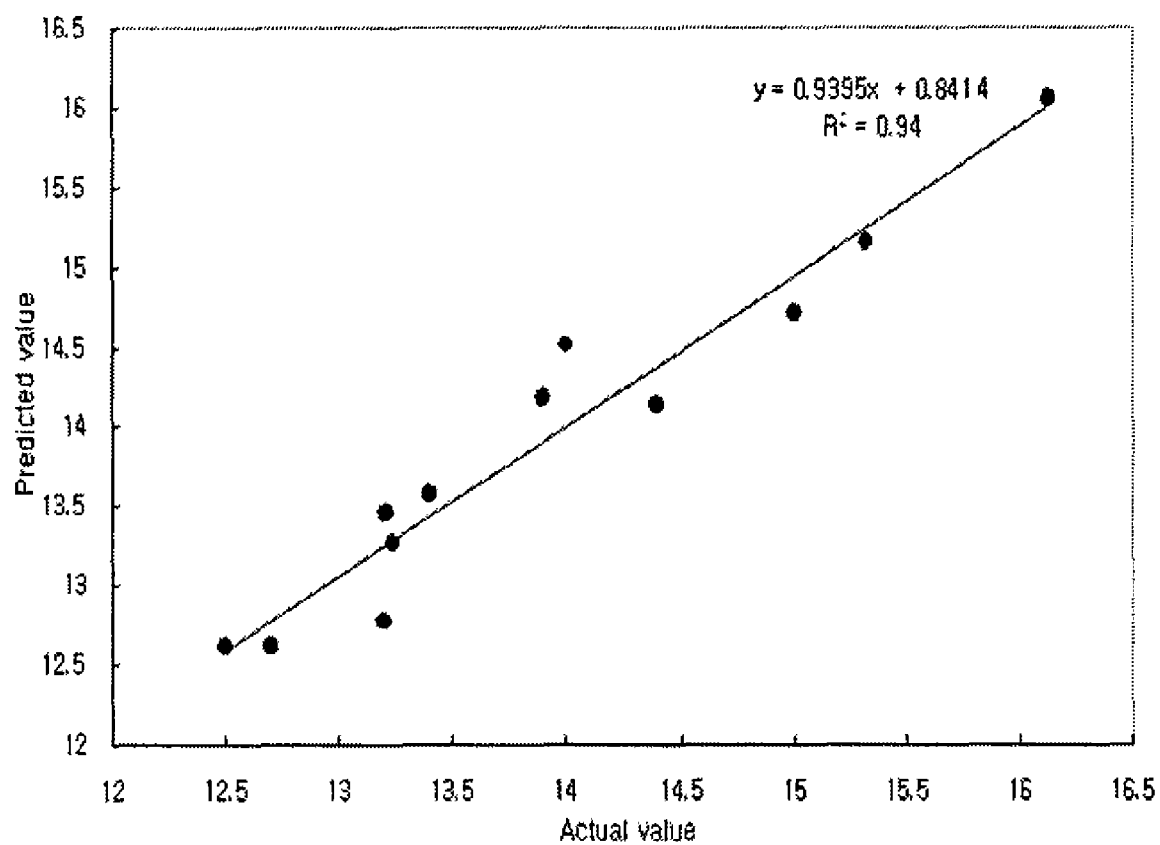
FIG. 11 a graph representing a result obtained by examining total solids of milk according to the embodiment of the present invention.

FIG. 11 is a graph representing a result obtained by examining total solids according to the embodiment of the present invention. Since $R^2$ is 0.94 and the calibration curve has a nearly linear configuration, the measured value of the total solids is reliable. Therefore, a numerical value of the total solids of milk can be estimated through the measured value of the total solids.

Figure 12:
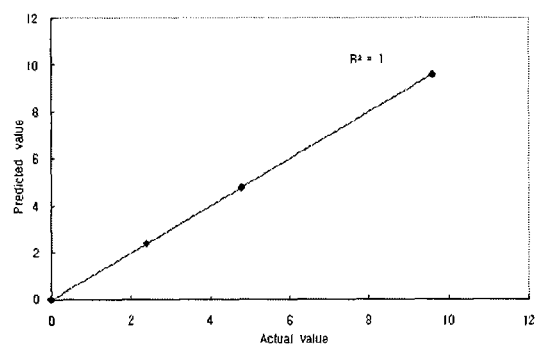
FIG. 12 a graph representing a result obtained by examining antibiotics of milk according to the embodiment of the present invention.
Figure 12:
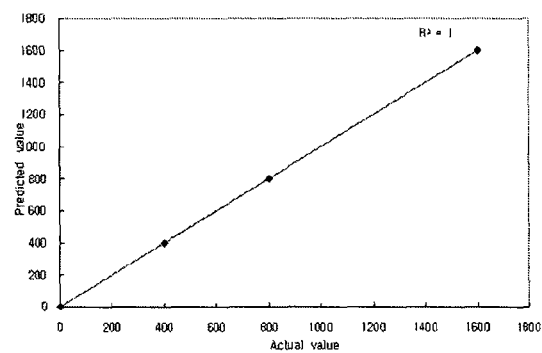
Figure 12:
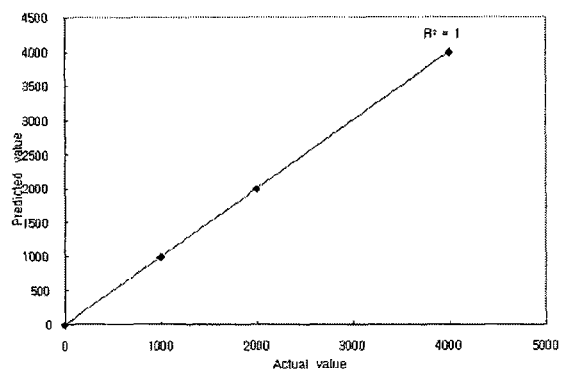
Figure 12:
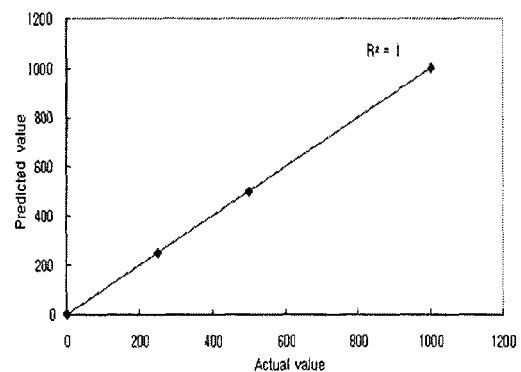

FIG. 12 is a graph representing a result obtained by examining antibiotics of milk according to the embodiment of the present invention. The $R^2$ of four representative antibiotics including PPS injection (penicillin G, beta-lactam based, A), tylocetin (chloramphenicol, B), terramycin (tetracycline, C), sulfa-40 (sulfadimethoxine sodium, D) is 1, and the calibration curve is almost linear, the measured value of the antibiotics is reliable. Therefore, a numerical value of the antibiotics of milk can be estimated through the measured value of the antibiotics.

Figure 13:
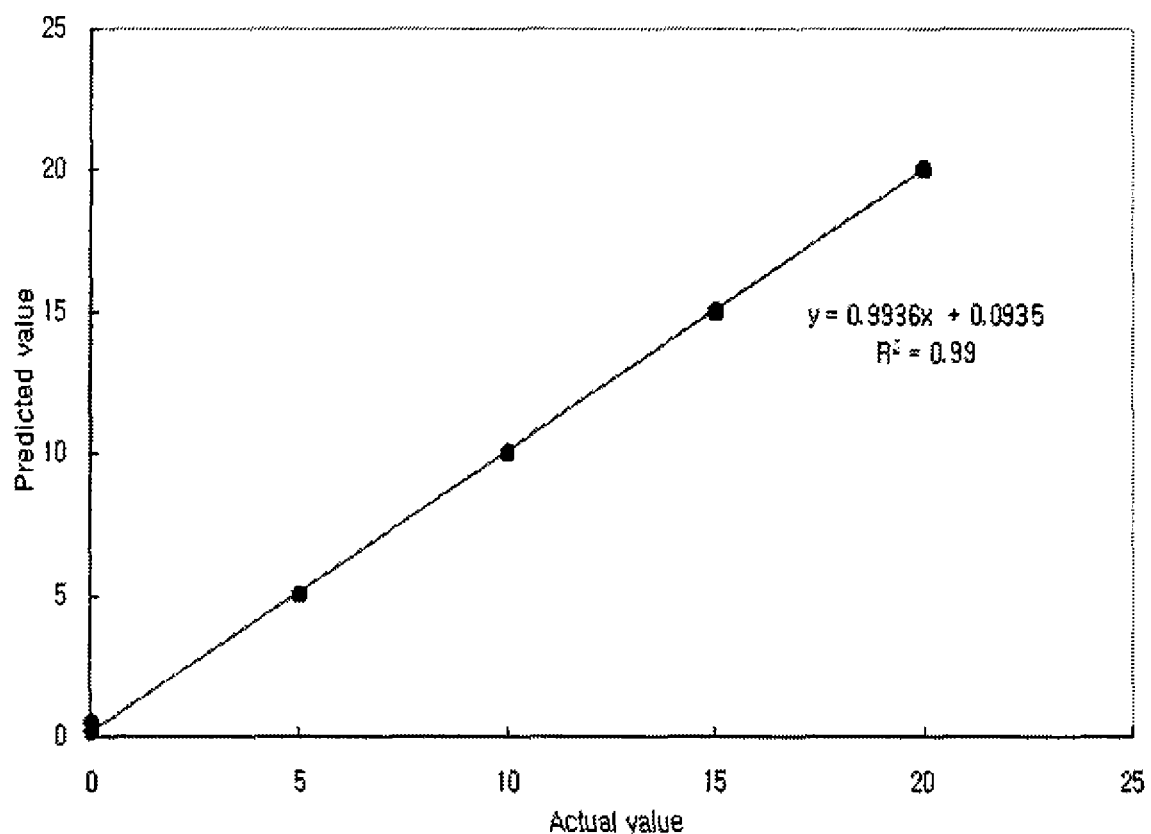
FIG. 13 a graph representing a result obtained by examining melamine of milk according to the embodiment of the present invention.

FIG. 13 is a graph representing a result obtained by examining melamine of milk according to the embodiment of the present invention. Since $R^2$ is 0.99 and the calibration curve has a nearly linear configuration, the measured value of the melamine is reliable. Therefore, a numerical value of the melamine of milk can be estimated through the measured value of the melamine.

Although few embodiments of the present invention have been shown and described, it would be appreciated by those skilled in the art that changes may be made in these embodiments without departing from the principles and sprit of the invention, the scope of which is defined in the claims and their equivalents.

What is claimed is:

1. An apparatus for analyzing milk by examining specific components of milk, the apparatus comprising:
    a body connected to a power supply unit installed at an outside of the body, provided at an outer surface thereof with a monitor for outputting measured data, a power button for turning on/off power and an operating button for run, and formed at an upper end thereof with a cell introduction hole through which a sample cell is inserted;
    a lamp power, which is installed in the body and operates when the operating button is switched on;
    a plurality of lamp fixing brackets, which are installed in the body and equipped with halogen lamps connected to the lamp power to generate beam;
    a sample fixing part, which is disposed corresponding to the cell introduction hole to mount the sample cell thereon and is installed at a side of the lamp fixing bracket;
    a monochromator, which is mounted at a side of the sample fixing part and includes a filter slit type tube having slits formed at both sides thereof to allow a predetermined amount of beam to pass therethrough, a rotary plate, which is provided with a plurality of interference filters and is installed in the filter slit type tube, and a drive motor connected to the rotary plate;
    a detector, which is mounted at a rear surface of the filter slit tube to detect incident monochromatic light; and
    a processing unit, which is connected to the detector to transfer an electric signal output from the detector to the monitor as data.

2. The apparatus as claimed in claim 1, further comprising an amplifier interposed between the detector and the processing unit.

3. The apparatus as claimed in claim 1, further comprising a printing button formed at the outer surface of the body.

4. The apparatus as claimed in claim 1, wherein the rotary plate includes six interference filters that are arranged in a circumference direction of the rotary plate, and the interference filters have wavelength bands of 830 nm, 850 nm, 880 nm, 930 nm, 1200 nm (long pass filter) and 1100 nm (short pass filter), which are representative wavelength bands of milk protein, milk sugar, somatic cells, butterfat, MUN (milk urea nitrogen), total solids, antibiotics and melamine, respectively.

* * * * *